United States Patent [19]

Clark et al.

[11] Patent Number: 5,312,992
[45] Date of Patent: * May 17, 1994

[54] PROCESS FOR REMOVING SULFUR FROM ORGANIC SULFIDES

[75] Inventors: Roger T. Clark, Pottstown; Michael J. Lindstrom, Downington; Glenn T. Carroll, Jeffersonville, all of Pa.; Jeffrey H.-G. Yen, Woolwich, N.J.

[73] Assignee: Elf Atochem North America, Inc., Philadelphia, Pa.

[*] Notice: The portion of the term of this patent subsequent to Feb. 25, 2009 has been disclaimed.

[21] Appl. No.: 780,608

[22] Filed: Oct. 23, 1991

Related U.S. Application Data

[62] Division of Ser. No. 357,399, May 26, 1989, Pat. No. 5,091,593.

[51] Int. Cl.$^5$ ............................................ C07C 319/22
[52] U.S. Cl. ...................................... 568/21; 568/22; 568/23; 568/25; 568/69
[58] Field of Search .................. 568/21, 22, 23, 25; 208/226, 237, 238, 248, 249

[56] References Cited

U.S. PATENT DOCUMENTS 3,188,293 6/1965 Bacon et al. .................. 208/245
4,127,470 11/1978 Baird et al. .................... 208/226
4,827,040 5/1989 Labat et al. ..................... 568/21
5,091,593 2/1992 Lindstrom et al. ............ 568/22

FOREIGN PATENT DOCUMENTS 086567 2/1978 Japan .

OTHER PUBLICATIONS

Dowling et al., "Regeneration of Loaded Dimethyl Disulfide Based Sulfur Solvent", Alberta Sulfur Research Limited, Quarterly Bulletin, vol. XXI, No. 3&4, pp. 30–52 (Oct. '84–Mar. '85).
Pickering, T. L. et al., "Disproportionation of Organic Polysulfides", J. Amer. Chem. Soc., (1967) 89, pp. 2364–2367.
Kende, I. et al., "The Dissociation Energy of the Tetrasulfide Linkage" J. Amer. Chem. Soc., (1965) 87, p. 55.
Grant, D. et al., "Exchange of Parts between Molecules at Equilibrium", J. Amer. Chem. Soc. (1964) 86 pp. 3012–3017.
Nelander, B. et al., "Cogwheel Effect in Dialkyl Disulfides" J. Amer. Chem. Soc., 94 (1972) pp. 3576–3577.
Reid, E. E., "Organic Chemistry of Bivalent Sulfur" Chem. Pub. Co., N.Y., (1960) 3 p. 391.
Harpp, D. N. et al., "Reaction of Trialkyl Phosphites with Organic Trisulfides", J. Org. Chem. (1979), 44 No. 23, pp. 4140–4144.

Primary Examiner—Marianne M. Cintins
Assistant Examiner—Margaret J. Page

[57] ABSTRACT

A process for removing sulfur from an organic sulfide containing three or more chemically bound sulfur atoms is disclosed wherein said sulfide is contacted with a defined catalyst at elevated temperature to increase the disproportionation rate and the corresponding sulfide of lower sulfur rank is continuously removed from the reaction zone.

18 Claims, 2 Drawing Sheets

PROCESS FOR REMOVING SULFUR FROM ORGANIC SULFIDES

This is a divisional of copending application Ser. No. 07/357,399 filed on May 26, 1989 now U.S. Pat. No. 5,091,593.

BACKGROUND

This invention relates to a process for the removal of sulfur from organic sulfides by disproportionation. More particularly, it relates to the use of specified catalyst systems at elevated temperature to effect disproportionation of organic sulfides containing three or more chemically bound sulfur atoms.

PRIOR ART

In the processing of sour-gas wells, sulfur may form deposits that can plug the well and cease production. A variety of solvents have been used to dissolve sulfur plugs in the well or associated flow lines by passing such solvents in contact with these plugs. For example, carbon disulfide, mineral and spindle oils and aqueous alkylamines have been employed as the solvents.

Dialkyl disulfides, either alone or blended with dialkyl sulfides (U.S. Pat. No. 3,531,160) have become the sulfur solvent of choice. During production of the sour-gas well, the dialkyl disulfide can be introduced into the well where it will react with sulfur and form dialkyl polysulfides whose range of contained sulfur atoms can greatly exceed 2, in particular, 3 to 11. For this process to be economical, it is desirable to remove most or all of the incorporated sulfur so that the regenerated solvent can be reinjected downhole. A process for the removal of sulfur from organic polysulfides is also useful for any commercial operation where sulfur deposits may form requiring the use of large volumes of sulfur solvent.

The publication of Dowling, Lesage, and Hyne ("Regeneration of Loaded Dimethyl Disulfide Based Sulfur Solvent", Alberta Sulfur Research Limited Quarterly Bulletin, Vol. XXI, No. 3 and 4, pp 30–52, October - March 1985) discloses the regeneration of dimethyl disulfide (DMDS) by stripping sulfur from dimethyl polysulfide (DMPS) in a batch operation with alkali metal and ammonium hydrosulfides and sulfides, preferably sodium sulfide. In the same publication (p 34–36), a process is disclosed for regenerating DMDS by distillation of DMPS to give good recoveries of DMDS but poor quality sulfur. When the distillation of DMPS was carried out in the presence of SiO, no improvement in the process was observed.

French Patent Application 2,579,203 discloses the use of amines to remove sulfur from polysulfides by heating the dialkyl polysulfide with an aqueous solution of the amine to form water soluble ammonium polysulfides, which can then be converted to the original amine and sulfur.

Thermal degradation of dialkyl polysulfides to polysulfides of lower sulfur rank are known; however, reaction times are too long for a viable commercial process. For example, dimethyl tetrasulfide disproportionates to a mixture consisting of 49% dimethyl tetrasulfide, 31% dimethyl trisulfide, 13% dimethyl pentasulfide, and 7% dimethyl hexasulfide after 5 hrs of heating at 80° C. The presence of free radicals was found to inhibit higher polysulfide formation.

SUMMARY OF THE INVENTION

This invention is a process for decreasing the sulfur content of an organic sulfide containing at least three chemically bound sulfur atoms, and preferably having the formula:

$$RSS_aSR^1$$

wherein R and $R^1$ are independently alkyl, aryl, alkaryl, hydroxyalkyl, or alkoxyalkyl groups and a is an average number greater than 0 but no greater than 13, comprising contacting said organic sulfide at elevated temperature with a catalyst having the capacity and in an amount sufficient to increase the rate of disproportionation of said organic sulfide to thereby produce sulfur and a sulfide of reduced sulfur rank, and continuously removing said sulfide of reduced sulfur rank from the reaction zone.

DETAILED DESCRIPTION OF THE INVENTION

Figure 1:
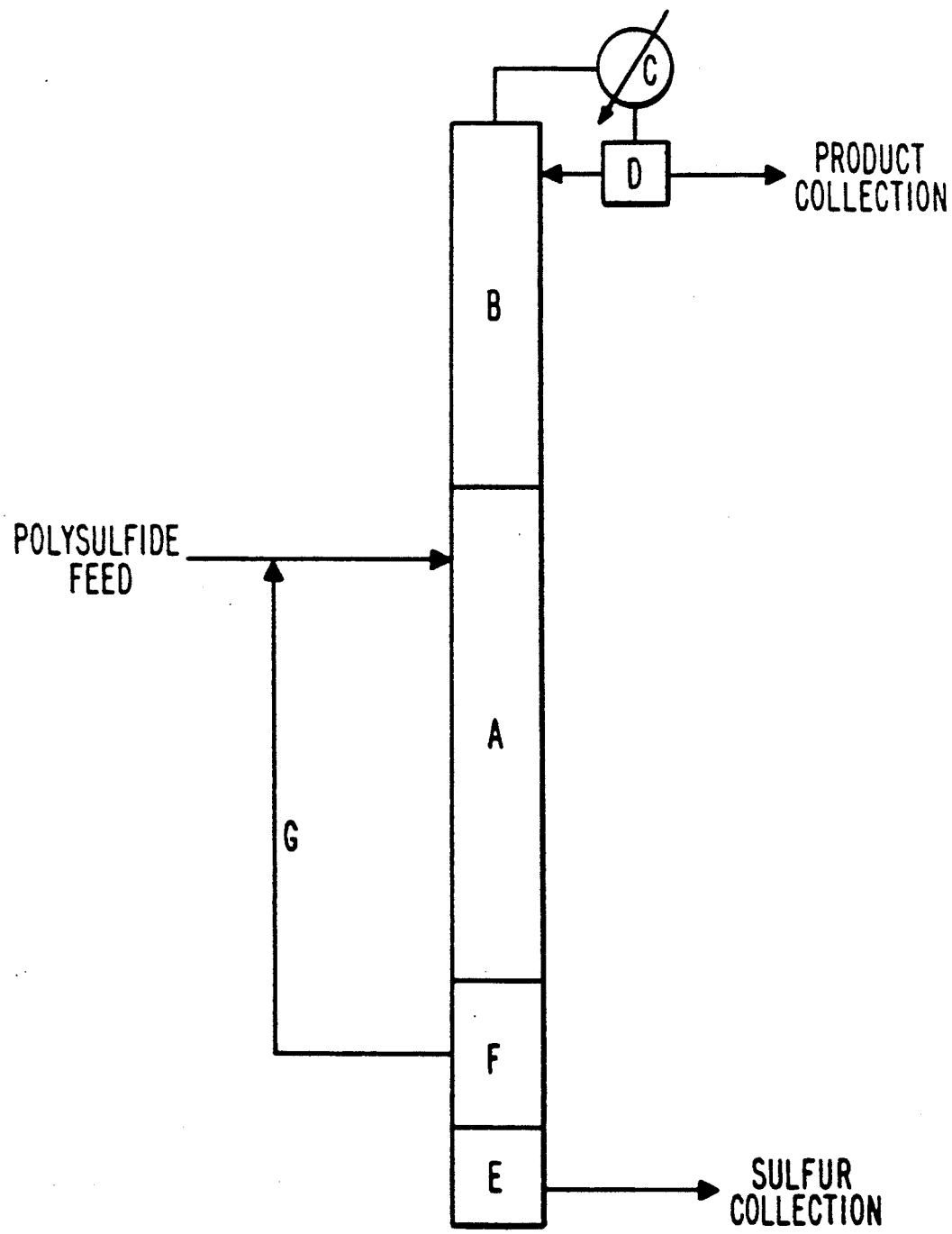
FIG. 1 of the drawing is a schematic representation of a reactor for the practice of this invention.

In the processing of sour-gas wells, a solvent, for example, dimethyl disulfide, is continuously injected downhole to dissolve or prevent sulfur plugs. The need to remove the sulfur from the produced dimethyl polysulfide and thereby regenerate a sulfide of lower sulfur rank for reinjection downhole is dictated by economic considerations. This invention serves to lower the sulfur rank of a given organic sulfide so that it can be re-used to take up more sulfur.

The present invention is a process for decreasing the sulfur content of an organic sulfide containing at least three (3) chemically bound sulfur atoms by contacting said organic sulfide at an elevated temperature with a catalyst having the capacity and in an amount sufficient to increase the rate of disproportionation of said organic sulfide to thereby produce sulfur and a sulfide of reduced sulfur rank, and continuously removing said sulfide of reduced sulfur rank from the reaction zone. It is an advantage of the process of the invention that the use of catalysts to increase the rate of disproportionation of the polysulfides allows the use of lower temperatures. Furthermore, if the disulfide or low-sulfur-rank polysulfide is continuously removed from the reaction zone, the sulfur that was previously bound in the polysulfide is released and is left behind for recovery.

The organic sulfide to be treated in the process is preferably a mixture of compounds having the formula:

$$RSS_aSR^1$$

where R and $R^1$ are independently alkyl, aryl, alkaryl, hydroxyalkyl or alkoxyalkyl groups wherein the alkyl moieties have from 1 to 24, more preferably 1 to 8, carbon atoms and a is an average number greater than 0 but no greater than 13. The value of a represents the average number of internal sulfur atoms in a given organic sulfide composition and not the maximum number of sulfurs for any one species in the composition.

The preferred catalyst or catalyst system for use in the process include the following: alkyl, cycloalkyl, substituted alkyl, aryl or alkaryl amine or polyamine wherein any of the alkyl moieties has from 1 to 24 carbon atoms.

Suitable amine catalysts are those selected from the group.

$$R^3R^4R^5N$$

where in $R^3$, $R^4$, and $R^5$ are independently H, C—C alkyl, cycloalkyl, aryl, or alkaryl, or hydroxyalkyl groups, $R^3$ and $R^4$ may also comprise, with the nitrogen, a heterocyclic ring such as pyrrolidine, piperidine, morpholine, or pyridine. If the heterocycle is pyridine, the nitrogen contains only two substituents.

Also suitable are polyamines of the type represented by the formula:

$$R^6R^7N(CH_2\overset{R^8}{\overset{|}{C}}H\overset{R^9}{\overset{|}{N}})_xCH_2\overset{R^{10}}{\overset{|}{C}}HNR^{11}R^{12}$$

where $R^6$, $R^7$, $R^8$, $R^9$, $R^{10}$, $R^{11}$, and $R^{12}$ are independently H, $C_1$–$C_{24}$ alkyl, cycloalkyl, aryl, or alkaryl groups and x is an integer from 0 to 25. $R^6$ and $R^7$, or $R^{11}$ and $R^{12}$, may also comprise, with the nitrogen, a heterocyclic ring such as pyrrolidine, piperidine, or morpholine. Bicyclic amines such as 1,4-diazabicyclo[2.2.2]octane, 1,5-diazabicyclo[4.3.0]non-5-ene and 1,8-diazabicyclo[5.4.0]undec-7-ene are also suitable catalysts.

Suitable polyalkyleneoxyamines or -polyamines are specified in U.S. Pat. No. 4,804,485 issued Feb. 14, 1989, and are exemplified by, but not limited to, the Jeffamine® product line of Texaco, Inc.

It is preferable that the amine have a boiling point sufficiently greater than that of the disulfide/low-rank polysulfide product such that they may be conveniently separated.

The amine catalyst may be used alone or dissolved in a solvent which is an organic polysulfide or liquid hydrocarbon wherein the solvent has a higher atmospheric boiling temperature than the organic sulfide of reduced sulfur rank which is recovered in the process. The organic polysulfide solvent is preferably as described for the sulfide to be treated in the process and the liquid hydrocarbon will include, for example, paraffinic hydrocarbons having a boiling point sufficiently greater than that of the sulfide of reduced sulfur rank to allow for convenient separation.

Additionally, the amine catalyst may be carried or mounted on a solid, inert support material or on an active solid catalyst including silica, alumina, silica-alumina, zeolite, vanadia, chromia, thoria, magnesia, titania, complex compounds thereof and mixtures thereof. Inert supports which may be used include, for example, solid regular and irregular shaped, porous particulates, Raschig rings, Pall rings, glass helices and pellets, Berl saddles and the like. The supports are impregnated or coated with the amines either as straight liquids or diluted with a solvent or liquid dilutant. Coating or impregnation can be accomplished external of the reactor or in the reactor by feeding the amine or solution thereof to the support in the heated reactor. Optionally, make up catalyst may be fed with the organic sulfide to supplement the catalyst on the support. When mounted on a support material, the catalyst is generally used in the form of a heated bed in the process through which the organic sulfide is passed to effect disproportionation.

Another group of preferred catalyst or catalyst systems is alkali metal, alkaline earth metal or ammonium hydroxide, oxide, ($C_1$–$C_4$) alkoxide, hydrosulfide, sulfide, thiosulfate or mercaptide. These catalyst materials may be used in the process either alone or mounted on a support or dissolved in a solvent which is either an organic polysulfide or liquid hydrocarbon where the solvent has a higher atmospheric boiling temperature than the sulfide of reduced sulfur rank to be recovered. These solvents are those described herein as useful for the amine catalyst. Additionally, these catalysts may be used in conjunction with up to 10 wt.% of an amide-type compound. For example, dialkyl formamide, dialkyl acetamide and dialkyl butamide may be used to enhance the activity of the catalyst. When used alone or on a support this catalyst material may be employed in the form of a heated bed through which the organic sulfide is passed. The active catalyst may be mounted on inert or active supports as described for the aforementioned amine catalysts by dissolving the catalyst in a solvent such as water or an alcohol and impregnating or coating the support with the solution.

Suitable alkali or alkaline earth metal hydroxides, oxides, alkoxides, hydrosulfides, sulfides, thiosulfates, or mercaptides include simple alkali and alkaline earth metal hydroxides, oxides, hydrosulfides, sulfides and thiosulfates, as well as the alkali and alkaline earth metal salts of $C_1$–$C_{24}$ alkyl, aryl, alkaryl, and hydroxyalkyl alcohols and mercaptans.

Suitable ammonium salts are the hydroxide, oxide, hydrosulfide, sulfide, and $C_1$–$C_{24}$ alkyl, aryl, alkaryl, and hydroxyalkyl alkoxide and mercaptide salts of nitrogen-based cations of the general structure $$R^{13}R^{14}R^{15}R^{16}N+$$

where in $R^3$, $R^4$, $R^{15}$ and $R^{16}$ are independently H, $C_1$–$C_{24}$ alkyl, cycloalkyl, aryl, alkaryl, or hydroxyalkyl groups. $R^{13}$ and $R^{14}$ may also comprise, with the nitrogen, a heterocyclic ring such as pyrrolidine, piperidine, or morpholine.

Also suitable are the ammonium salts derived from polyamines of the type represented by the formula:

$$R^{17}R^{18}N(CH_2\overset{R^{19}}{\overset{|}{C}}H\overset{R^{20}}{\overset{|}{N}})_xCH_2\overset{R^{21}}{\overset{|}{C}}HNR^{22}R^{22}$$

where in $R^7$, $R^8$, $R^9$, $R^{20}$, $R^{21}$, $R^{22}$, and $R^{23}$ are independently H, $C_1$–$C_{24}$ alkyl, cycloalkyl, aryl, or alkaryl groups and x is an integer from 0 to 25. $R^{17}$ and $R^{18}$, and $R^{22}$ and $R^{23}$ may also comprise, with the nitrogen, a heterocyclic ring such as pyrrolidine, piperidine, or morpholine.

The ammonium ions derived from bicyclic amines such as 1,4-diazabicyclo[2.2.2]octane, 1,5-diazabicyclo[4.3.0]non-5-ene, and 1,8-diazabicyclo(5.4.0]undec-7-ene are also suitable.

Also suitable are ammonium ions derived from polyalkyleneoxyamines or -polyamines as specified in the aforementioned U.S. Pat. No. 4,804,485, which are exemplified by, but not limited to, the Jeffamine(b product line of Texaco, Inc.

Suitable polysulfides are polysulfides with equal or greater molecular weight alkyl, aryl, or alkaryl substituents than the polysulfide in the feed.

Another group of preferred catalyst or catalyst systems includes, but is not limited to, activated silica, alumina, silica-alumina, zeolite, vanadias, chromia, thoria, magnesia, titania, complex components thereof and mixtures thereof. These materials may be used in the process either alone or in mixtures with or as carriers for other catalysts, for example, amines and alkali or alkaline earth metal hydroxides, oxides, alkoxides, hydrosulfides, sulfides, thiosulfates or mercaptides. Commercially available materials of this type are, for example, Types X, Y and L zeolites manufactured by Union Carbide Corporation and described in U.S. Pat. No. 4,568,767; Silicalite ® manufactured by Union Carbide Corporation; and ZSM-5 ® silica zeolites sold by Mobil Corporation.

Where the catalyst is predissolved in the organic sulfide to be treated and the sulfide fed to a heated reactor packed with inert material, preferred catalysts are those typically used in catalyzing sulfur-uptake from sulfur-rich systems. These catalysts include alkylamines, blends of sodium hydrosulfide and dialkylamides (dimethyl formamide) and one or more polyalkyleneoxyamines or polyalkyleneoxypolyamines as disclosed in the aforementioned U.S. Pat. No. 4,804,485. When the catalyst is predissolved in the organic sulfide to be treated in the process, catalyst concentrations ranging from an amount at least sufficient to accelerate disproportionation of the organic sulfide, usually at least 0.01% of the catalyst, based on the weight of the sulfide-catalyst composition, up to about one (1) part per part by weight of the organic sulfide feed may be used.

FIG. 1 of the drawings shows a schematic diagram for a reactor configuration to practice this invention. It is presented to illustrate this invention and is not intended to limit its scope. Many variations of this configuration are possible.

The organic polysulfide to be treated is fed into the reactor system either immediately above or directly into Reactor A. Reactor A contains one or more solid catalysts as previously described or, if the polysulfide feed contains the catalyst predissolved in it, may contain an inert packing material or trays. The temperature in Reactor A can range from 120°–250° C. Preferably, a temperature gradient exists such that the top of Reactor A is held at 120°–140° C. and the bottom is held at 160°–220° C. The preferred mole velocity of the polysulfide in zone B depends upon the lability of the polysulfide, the temperature profile of Reactor A and the process requirements. Typical mole velocities may be in the range of 10–200 gram-moles feed/kg. catalyst/24-hour day, although values outside of this range are still within the scope of the invention. Preferred are mole velocities in the range of 50–150 gram-moles/kg catalyst/24-hour day.

As the polysulfide decomposes, volatiles enter fractionator B. Fractionator B may be a packed or trayed distillation column. The volatile products are fractionated with disulfide/low-rank polysulfide being condensed in condenser C and collected in reflux accumulator D. Heavier materials, condensed in the column, are returned to Reactor A. Subatmospheric or superatmospheric pressures may be used in Reactor A and fractionator B, but pressures ranging from about 100 mm Hg to atmospheric or slightly higher and preferred for ease of operation and economy of equipment.

Produced sulfur is collected in receiver E, preferably as a liquid, and sent for further processing or to storage.

Optionally, a second recycle-collection zone, F, may be used to separate unreacted polysulfide and/or hydrocarbon solvent from the collected sulfur. These materials can be recycled to Reactor A through recycle line G.

In the practice of the invention it is not necessary for the reactor, distillation column, and sulfur and recycle-collection zones to be integral segments of a single column. Practice of this process using discrete process vessels is well within the scope of the invention. In one embodiment of the process of the invention, illustrated in FIG. 2, which is particularly suitable for use with soluble catalysts, reactor A and collection zones E and F, as described above for FIG. 1, become integral zones in a single continuous stirred tank reactor (CSTR), with the reaction zone being separated from the collection zones by an internal separation device, and the fractionation zone B becomes a stand-alone or multi-towered distillation train.

Figure 2:
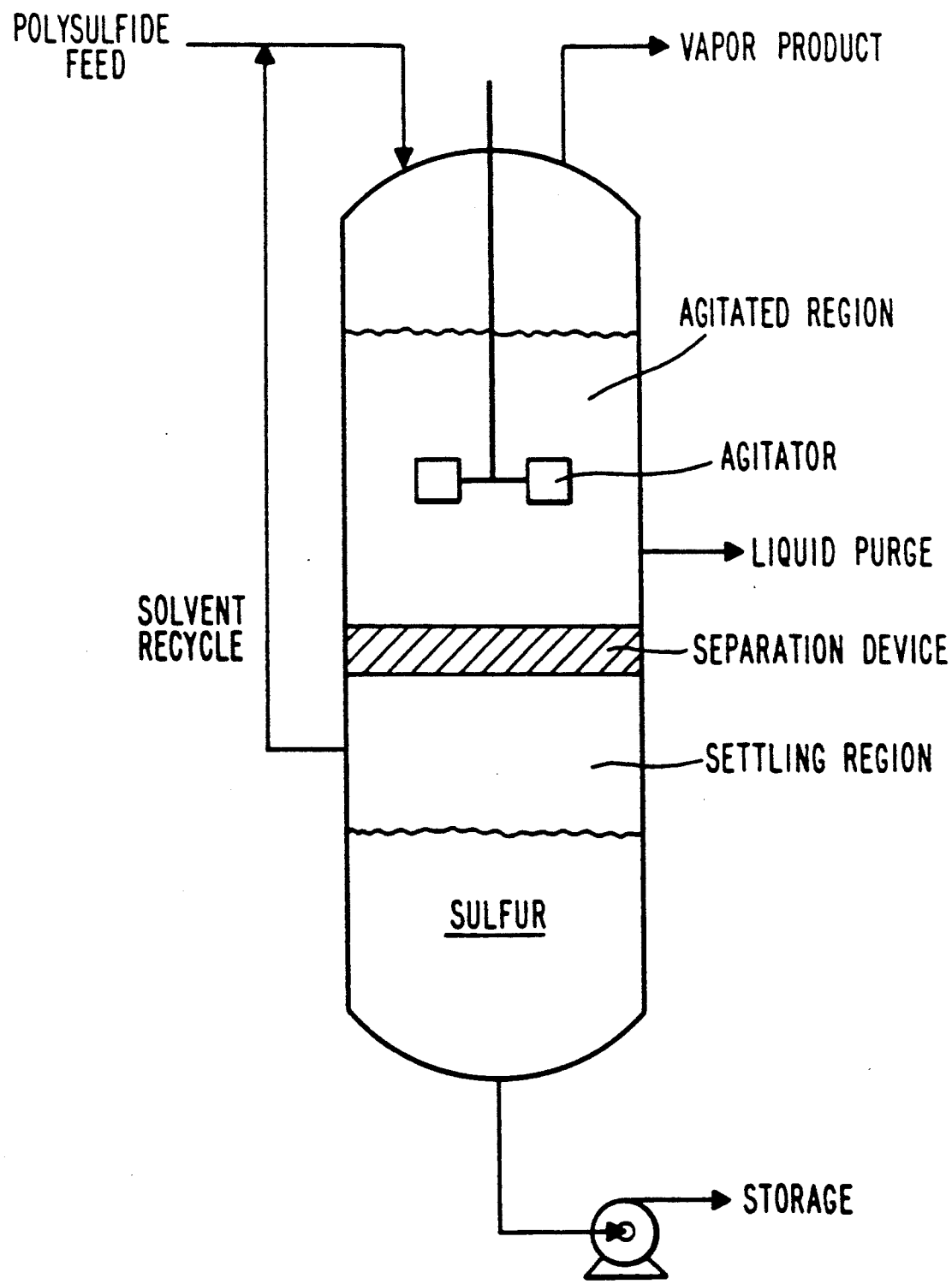
FIG. 2 is a diagramatic view of one embodiment of a reactor for the practice of this invention.

The area above the separation device shown in FIG. 2 is an agitated region where the reactions occur. Molten sulfur is formed in this reaction region. Because of density differential, molten sulfur settles downward and, after flowing through the separation device, accumulates in the bottom of the settling region. The settling region will not be disturbed by the agitation in the reaction region.

Should the agitation in the reaction region, as required by the reaction, become too vigorous, a secondary separation device, such as a holed plate, is recommended to be placed atop of the primary separation device. The function of the secondary separation device is to create a less-turbulent region for the settling of molten sulfur.

The separation device can be holed plate(s), packed rings or grids, mesh screens, etc. Optionally, packed heating coils can also be used as the separation device. In the case of mesh screens, the construction material of the separation device should be carefully selected such that the material itself can enhance the agglomeration or coagulation of sulfur particles.

While continuous operation is preferred, this configuration can also be used for the batch processing of organic polysulfides. In this case, the organic polysulfide is added to the catalyst mixture and the reactor is heated to the desired temperature. After the distillation stops, the molten sulfur layer can be drained off. Alternatively, the contents of the reactor can be cooled and the precipitated sulfur collected by filtration.

In the practice of this invention, it may be convenient to perform the disproportionation in several stages. For example, in the case of a heated fixed-bed reactor, one stage is held at a given set of temperatures and pressures to effect most of the reaction, while a second, or third stage, is held at typically a higher temperature, to disproportionate the remaining polysulfide from the produced molten sulfur. In this way prolonged heating and decomposition to undesirable products of the polysulfides Can be avoided.

Additionally, the introduction of inert gases, like $N_2$, at the bottom of the fixed-bed reactor can aid in the separation of the organic polysulfide from the formed sulfur and lead to better quality sulfur.

Decomposition products from the disproportionation reaction, like mercaptans, can be recycled by introduction into the catalyst bed below the reaction zone.

EXAMPLES

The dimethyl polysulfides (DMPS) used in the following examples were prepared as follows.

Dimethyl disulfide (DMDS) was catalyzed by preparing a composition of 0.39% by weight of Jeffamine® D230

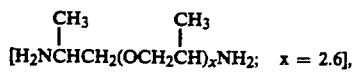
[$H_2NCHCH_2(OCH_2CH)_xNH_2$; x = 2.6], 0.44% Jeffamine® ED600

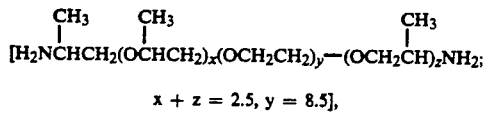
[$H_2NCHCH_2(OCHCH_2)_x(OCH_2CH_2)_y-(OCH_2CH)_zNH_2$;

x + z = 2.5, y = 8.5], 0.5% by weight Jetamine® PE13 [$C_{13}H_{27}OCH_2CH_2CH_2NH_2$] and a remainder of DMDS. The catalyzed DMDS was activated by bubbling with $H_2S$ for three (3) minutes. The activated composition was called "catalyzed DMDS".

In 100 g of catalyzed DMDS was dissolved portionwise 80.0 g of powdered sulfur with stirring. This polysulfide is referred to as "80%-Loaded DMPS".

A sample of 150% loaded DMPS was prepared similarly except that 150 g of powdered sulfur was dissolved in 100 g of catalyzed DMDS.

DMPS that is "free" of catalysts was prepared as follows. A 100 g sample of 80% or 150% loaded DMPS was vigorously washed with 100 mL of 10% HCl, followed by a water wash and drying over $MgSO_4$. The resulting clear yellow polysulfides were shown to be free of catalysts by analysis.

EXAMPLE 1

Disproportionation of DMPS in the presence of catalysts.

To 25 g of 80% loaded DMPS that contained catalyst was added to 25 g of 150% loaded DMPS that also contained catalyst in a 150 mL round-bottom flask fitted with a distillation head and an internal temperature probe. The 150% loaded DMPS was present to simulate the approximate composition of a reactor during continuous operations.

The contents of the flask were heated to 140° C. at 100 mmHg over a 2 hour period. Two fractions were obtained boiling at 55°–57° C. (3.0 g) and 75°–75° C. (13.8 g). Fraction 1 consisted of 1.29% methyl mercaptan (MeSH), 95.0% dimethyl disulfide (DMDS), and 4.3% dimethyl trisulfide (DMTS); Fraction 2 (13.8 g) contained 0.66% MeSH, 83.7% DMDS, and 15.0% DMTS [by gas chromatography (GC) analysis]. This corresponds to a 67% recovery of DMDS based on the entire contents of the pot. On cooling, the pot residue solidified. The dark solid was triturated with 50 ML 1 : 1 hexane/$CHCl_3$ and collected to yield 20.4 g of sulfur (m.p. 107°–111° C.).

This illustrates the efficiency of using the contained sulfur-dissolution catalysts to affect the disproportionation of organic polysulfides.

EXAMPLE 2

Disproportionation of DMPS in the absence of catalysts

The procedure described in Example 1 was repeated except that catalyst-free 80% and 150% loaded DMPS were used. Only 2.5 g of distillate was collected (99% DMDS) and no precipitation of sulfur was observed in the pot upon cooling.

This example demonstrates the need for catalysts for the disproportionation reaction to occur smoothly.

EXAMPLE 3

Disproportionation of DMPS with an amine catalyst

The sample of (~500 mL) of DMPS used in this work was purified by washing in a separatory funnel with three 500 ml portions of 5% sulfuric acid, followed by three 500 ml portions of distilled water. The resulting amber liquid was dried over magnesium sulfate. The resulting DMPS was shown by analysis to be 80% sulfur loaded.

Into a 100 mL round bottom flask equipped with a magnetic stirrer, a Vigreux distillation column, vacuum adapter and water cooled condenser, was added 24.5 g of a high boiling hydrocarbon solvent (with a boiling range of 170°–220° C.). The system pressure was maintained at 100 mm Hg with a vacuum pump, and the flask was heated to 120°–125° C. with an oil oath. Over a period of two hours, 11.9 g of DMDS, equivalent to 85% of the theoretical recovery, was distilled from the system. During distillation, the liquid sulfur phase separated into a bottom layer and was drawn off. The distillate was analyzed by GC, and was found to consist of 99.2% DMDS, 0.6% MESH, 0.1% DMTS (dimethyltrisulfide), and 0.1% hydrocarbon solvent. The sulfur layer was allowed to solidify and was analyzed and found to contain a maximum of 2% DMDS and trace quantities of amine and hydrocarbon, thus demonstrating the efficiency of amines as catalysts.

EXAMPLE 4

Disproportionation of DMPS using sodium hydrosulfide (NaSH) as the Catalyst

The reaction was carried out in the same equipment set-up and with the same quantity and quality of DMPS as specified in Example 3. In this case the catalyst was 0.29 g of NaSH, and no solvent was employed. During the course of the distillation, the solution briefly turned orange, and the NaSH dissolved.

By operating as in Example 3, a total of 9.80 g of DMDS was recovered by distillation. The distillate was analyzed by GC and consisted of 99.4% DMDS, 0.3% MESH and 0.3% DMTS. After distillation, the pot residue, which consisted largely of elemental sulfur and undistilled DMDS weighed 13.5 g. The recovery of DMDS from DMPS was 76% of theoretical, demonstrating the efficiency of NaSH as a catalyst.

EXAMPLE 5

Disproportionation of DMPS Using a Fixed-Bed Catalyst

In an apparatus consisting of a heated, vertical catalyst bed, a condenser and sulfur pot (See FIG. 1) was charged the indicated amount of catalyst (See Table 1). The catalyst bed was maintained at the indicated temperature by external heating. Catalyst-free DMPS prepared as before was introduced near the top of the catalyst bed at various flow rates. The internal pressure of the apparatus was maintained at 200 mm Hg for all experiments by a vacuum pump. The distillate was collected, weighed and analyzed to determine percent recoveries. Molten sulfur was collected in the sulfur pot at the bottom of the reactor. Results using various catalysts and reactor conditions are summarized in Table 1.

TABLE 1

| Catalyst | Catalyst Charge | Reactor Temp (°C.) | g DMPS fed/hr. | % DMDS Recovery |
| --- | --- | --- | --- | --- |
| LZ-Y52 Zeolite (Union Carbide) | 200 g | 140 | 84 | 85.6 |
| " | " | 140 | 294 | 59.5 |
| " | " | 160 | 193 | 100.9 |
| " | " | 180 | 293 | 87.3 |
| Silica-Alumina LA-100-3P (Akzo Chemie) | 200 g | 140 | 83.6 | 74.8 |
| " | " | 180 | 89.4 | 87.0 |
| Magnesia (MgO) | 194 | 160 | 84 | 91.0 |
| 4% NaOH on Berl Saddles | 163 | 160 | 72 | 88 |
| 2% NaOH on Macroporous Silica | 79 | 160 | 72 | 88 |

EXAMPLE 6

Disproportionation of DMPS Using a Fixed-Bed Catalyst

An apparatus of Example 5 is charged with 200 g of titania to form a catalyst bed which is maintained at 160° C. and the system pressure at 200 mm Hg while 190 g of DMPS is fed into a region near the top of the catalyst bed. As the reaction occurs, the distillate, which contains regenerated dimethyl disulfide, is collected and sent to storage for future use. The molten sulfur is removed from the bottom of the catalyst bed and is sent for further processing or stored.

EXAMPLE 7

Disproportionation of DMPS Demonstrating Recycle of Methyl Mercaptan

Into the apparatus of Example 5 charged with 200 g of a catalyst consisting of 198 g Berl saddles on which was impregnated 5.0 g NaOH, was continuously fed, at an approximate rate of 1.25 g/min., a total of 168.7 g DMPS and 20.0 g MeSH. The reaction temperature was held at 160° C. and the reaction pressure was 410 mm Hg. The distillate (99.5 g) was collected and gave the following analysis; 0.4% $H_2S$, 3.9% MESH, 2.1% $CS_2$, 38.4% DMDS, and 55.2% DMTS (dimethyltrisulfide). An additional dry ice trap positioned after the distillation receiver contained 7.2 g of a material with the following analysis; 0.29% $H_2S$, 1.9% MESH, 3.8% $CS_2$, 79.7% DMDS, and 14.2% DMTS. This corresponds to a 85.9% recovery of DMDS and an 80% conversion of MESH to DMDS.

We claim:

1. A process for decreasing the sulfur content of an organic sulfide which is one or more compounds having the formula:

$$RSS_aSR^1$$

where R and $R^1$ are independently alkyl, aryl, alkaryl, hydroxyalkyl or alkoxyalkyl groups wherein the alkyl moieties have from 1 to 24 carbon atoms and $a$ is an average number greater than 0 but no greater than 13, comprising contacting said organic sulfide at an elevated temperature with a catalyst having the capacity and in amount sufficient to increase the rate of disproportionation of said organic sulfide to thereby produce sulfur and a sulfide of reduced sulfur rank, and continuously removing said sulfide of reduced sulfur rank from the reaction zone.

2. The process of claim 1 wherein said catalyst is an alkyl, cycloalkyl, substituted alkyl, aryl or alkaryl amine or polyamine wherein any of the alkyl moieties has from 1 to 24 carbon atoms.

3. The process of claim 1 wherein said catalyst is:
a) an alkali metal hydroxide, oxide, alkoxide, hydrosulfide, sulfide, thiosulfate or mercaptide, or
b) an alkaline earth metal hydroxide, oxide, alkoxide, hydrosulfide, sulfide, thiosulfate, or mercaptide, or
c) an ammonium hydroxide, oxide, alkoxide, hydrosulfide, sulfide, thiosulfate or mercaptide.

4. The process of claim 2 wherein said catalyst is dissolved in a solvent which is an organic polysulfide or liquid hydrocarbon, said solvent having a higher atmospheric boiling temperature than said sulfide of reduced sulfur rank, and continuously removing said sulfide of reduced sulfur rank by distillation.

5. The process of claim 3 wherein said catalyst is dissolved in a solvent which is an organic polysulfide or a liquid hydrocarbon, said solvent having a higher atmospheric boiling temperature than said sulfide of reduced sulfur rank, and continuously removing said sulfide of reduced sulfur rank by distillation.

6. The process of claim 3 wherein said sulfide is passed through a heated bed of said catalyst.

7. The process of claim 6 wherein said catalyst is carried on a solid, inert support.

8. The process of claim 2 wherein said organic sulfide is passed through a heated bed of said catalyst carried on a solid, inert support.

9. The process of claim 2 wherein said organic sulfide is passed through a heated bed of said catalyst carried on silica, alumina, silica-alumina, zeolite, vanadia, chromia, thoria, magnesia, titania, complex compounds thereof or mixtures thereof.

10. The process of claim 6 wherein said catalyst is in admixture with silica, alumina, silica-alumina, zeolite, vanadia, chromia, thoria, magnesia, titania, complex compounds thereof, or mixtures thereof.

11. The process of claim 6 wherein said sulfide of reduced sulfur rank is continuously removed by distillation.

12. The process of claim 8 wherein said sulfide of reduced sulfur rank is continuously removed by distillation.

13. The process of claim 9 wherein said sulfide of reduced sulfur rank is removed by distillation.

14. The process of claim 2 wherein said organic sulfide is first admixed with said catalyst.

15. The process of claim 14 wherein the organic sulfide-catalyst admixture is passed through a heated bed of a solid, inert material.

16. The process of claim 14 wherein the organic sulfide-catalyst admixture is passed through a heated bed of an alkali metal, alkaline earth metal or ammonium hydroxide, oxide, alkoxide, sulfide, hydrosulfide, thiosulfate or mercaptide.

17. The process of claim 14 wherein the organic sulfide-catalyst admixture is passed through a heated bed of silica, alumina, silica-alumina, zeolite, vanadia, chromia, thoria, magnesia, titania, complex compounds thereof or mixtures thereof.

18. The process of claim 1 wherein sulfur is removed by recovery of a molten layer or solid precipitate thereof.

* * * * *